United States Patent [19]

Finch

[11] 4,079,072
[45] Mar. 14, 1978

[54] METHANATION PROCESS
[75] Inventor: Jack N. Finch, Bartlesville, Okla.
[73] Assignee: Phillips Petroleum Company, Bartlesville, Okla.
[21] Appl. No.: 741,643
[22] Filed: Nov. 15, 1976
[51] Int. Cl.$^2$ ............................................. C07C 1/04
[52] U.S. Cl. .......................... 260/449 M; 252/411 S; 252/460; 252/466 PT
[58] Field of Search ...................... 260/449 R, 449 M

[56] References Cited

U.S. PATENT DOCUMENTS

| | | | |
|---|---|---|---|
| 2,553,398 | 5/1951 | Atwell | 260/449.6 |
| 2,573,795 | 11/1951 | Lanning | 260/449.6 |
| 2,583,611 | 1/1952 | Sullivan | 260/449.6 |
| 2,608,568 | 8/1952 | Hogan et al. | 260/449.6 |
| 2,616,914 | 11/1952 | Riblett | 260/449.6 X |
| 2,711,419 | 6/1955 | Milbourne et al. | 260/449.6 |
| 3,488,171 | 1/1970 | Baker et al. | 260/449 M X |
| 3,615,164 | 10/1971 | Baker et al. | 260/449 M X |
| 3,787,468 | 1/1974 | Fleming et al. | 260/449 M |
| 3,842,121 | 10/1974 | Ichikawa et al. | 260/449 M X |
| 3,999,961 | 12/1976 | White et al. | 260/449 M |

FOREIGN PATENT DOCUMENTS 807,584   1/1959   United Kingdom ............ 260/449 M

OTHER PUBLICATIONS

Shultz et al., Bureau of Mines, Report of Investigation, 6974 (1967), pp. 1–9.

*Primary Examiner*—Howard T. Mars

[57] ABSTRACT

Methane is prepared by contacting carbon monoxide and hydrogen in the presence of a supported rhodium-containing catalyst promoted with uranium. In another embodiment, the methanation activity of supported rhodium-containing catalysts lost due to sulfur poisoning is restored by contacting the catalysts with a sulfur-free feed of carbon monoxide and hydrogen at a temperature of about 550° C for a period of time sufficient to substantially restore methanation catalyst activity.

11 Claims, No Drawings
}

METHANATION PROCESS

This invention relates to the production of methane. In accordance with one aspect, this invention relates to an improved catalyst system for the production of methane. In yet another of its aspects, this invention relates to a process for restoring methanation catalyst activity of sulfur-poisoned catalysts. In accordance with another aspect, supported rhodium-containing methanation catalysts, particularly when promoted with uranium, that have been sulfur-poisoned are contacted with a sulfur-free methanation feed at a temperature of about 550° C to restore methanation catalyst activity.

It is currently becoming of more interest to produce synthesis gases suitable for use as fuel gas, for both home and industry. Synthesis gas can be produced, for example, by steam reforming of hydrocarbons. If the reformed mixture is used as a fuel, the steam reformed product can be altered by the shift reaction to produce a $H_2/CO=3$ product which is then reacted to form methane and used as substitute natural gas. It has, therefore, become important to find improved processes for the production of methane by synthesis from carbon monoxide and hydrogen.

One of the problems encountered in the synthesis of methane from carbon monoxide and hydrogen is the presence of sulfur in many available feedstreams for the processes. The development of methanation catalysts that are less susceptible to sulfur poisoning than catalysts in current use can provide an overall increase in the production of methane during a given period of reaction. The present invention is directed to improved methanation catalysts and to the restoration of catalyst activity of sulfur-poisoned methanation catalysts.

Accordingly, an object of this invention is to provide improved methanation catalysts.

A further object of this invention is to provide an improved process for producing methane from carbon monoxide and hydrogen.

A further object of this invention is to provide a process for restoring catalyst activity of sulfur-poisoned methanation catalysts.

Other objects, aspects, and the several advantages of this invention will be apparent to those skilled in the art upon reading the specification and the appended claims.

In accordance with the present invention, a method is provided for producing methane which comprises contacting hydrogen with carbon monoxide in the presence of a supported rhodium-containing catalyst promoted with uranium.

In accordance with another embodiment of the invention, sulfur-poisoned methanation catalysts comprising supported rhodium-containing catalysts are restored for methanation activity by contacting the sulfur-poisoned catalysts with a sulfur-free feed of carbon monoxide and hydrogen at a temperature of about 550° C for a period of time to substantially restore the activity of the sulfur-poisoned catalysts.

In accordance with a further embodiment of the invention, supported rhodium-containing catalysts, particularly when promoted with uranium, exhibit good recovery from sulfur poisoning when the poisoned catalysts are contacted in situ at about 550° C with a sulfur-free methanation feed.

Methanation of synthesis gas comprising hydrogen and carbon monoxide, generally at a stoichiometric molar ratio of about 3:1, over supported rhodium-containing catalysts, is effected in this invention. It has been found that such catalysts when poisoned by a sulfur compound such as $CS_2$, $H_2S$, etc., can be restored in activity by contacting the catalysts under methanation conditions at about 550° C with a sulfur-free feed. By poisoning is meant that a sufficient amount of a sulfur compound has contacted that catalyst to suppress its methanation activity to a low level. The amount of sulfur compound added generally exceeds that required to cover the catalytic sites on the surface of the catalyst and in most cases is sufficient to form the metal sulfide or sulfides. Methane produced can be recovered from the effluent and used as synthetic natural gas or for other purposes, if desired. The synthesis gas feed can be made by conventional steam reforming of hydrocarbons, i.e., naphtha, and coal char, by blending hydrogen and carbon monoxide obtained from suitable refinery or chemical process streams, and the like.

The catalysts of this invention consist of rhodium supported on a refractory, particulate substrate selected from alumina, silica-alumina, Group II titanates such as calcium titanate, zinc titanate, and the like. Other Group VIII metals such as iron, cobalt, nickel, ruthenium, and palladium are not equivalent to rhodium in this invention.

The concentration of the rhodium in the catalysts, calculated as the metal, ranges from about 0.05 to about 5 weight percent, more preferably from about 0.1 to about 2 weight percent, and still more preferably from about 0.5 to about 1 weight percent, based on the weight of the metal plus support.

The concentration of the uranium promoter, when used, in the supported rhodium catalysts ranges from about 0.1 to about 10 weight percent, more preferably from about 0.5 to about 5 weight percent, and still more preferably from about 2 to about 4 weight percent, based on the weight of metal plus the rhodium plus the support.

The catalysts can be prepared by dry mixing or conveniently by impregnation of the particulate support with a solution or solutions of the metal compounds. The resulting mixtures can be dried in air, i.e., at 125° C, and calcined in air or hydrogen at an elevated temperature, i.e., about 400° C–600° C. It is presently preferred to charge the reactor with the desired amount of the catalyst and to heat it in a hydrogen stream just prior to conducting the methanation reaction.

Suitable metal compounds that can be used in preparing the catalysts include those soluble in water or in nonaqueous solvents such as, for example, alcohols, ethers, hydrocarbons, and the like. Exemplary rhodium compounds include the aminechloride, hydrated chloride, hydroxide, nitrate, oxide, sulfate, ammonium hexanitrorhodate, and the like. Exemplary uranium compounds include uranium sulfate, uranium tetrachloride, uranium trichloride, uranium trioxide, and such uranyl compounds as the acetate, carbonate, formate, nitrate, sulfate, and the like. Presently preferred compounds employed in preparing solutions for impregnation of the support are rhodium nitrate and uranyl nitrate.

The reaction temperatures employed in the practice of this invention range from about 200° C to about 600° C, more preferably from about 300° C to about 575° C, and most preferably about 550° C. The pressures employed can vary from about 0 to about 12,000 psig (0 to 82,700 kPa gage). The gaseous hourly space velocity (GHSV) of synthesis gas in terms of volumes of gas per volume of catalyst per hour can range from about 200 to about 10,000. Good results have been obtained at about 600 to about 5,000 GHSV.

In actual operation, the supported rhodium-containing catalyst, with or without promotion with uranium, is contacted with a feedstream comprising carbon monoxide and hydrogen and contacted with an effective amount of the catalyst under methanation reaction conditions such that a predominant amount of the carbon monoxide and hydrogen in the feedstream is converted to methane. In the event that the catalyst is poisoned due to the presence of sulfur in the feedstream, then the catalyst loses methanation activity; and, in accordance with one embodiment of the invention, the methanation catalyst activity can be restored by contacting the sulfur-poisoned catalyst with a sulfur-free methanation feed comprising carbon monoxide and hydrogen under methanation conditions of about 550° C, and the contacting is continued until the activity of the sulfur-poisoned catalyst is substantially restored so that methanation can be continued by contacting of the catalyst having restored activity with new methanation feed. The length of time that the sulfur-poisoned catalyst is contacted with the sulfur-free feed at about 550° C is continued for a period of time sufficient to substantially restore the activity of the catalyst, and this will ordinarily range from about ten to about 100 hours.

All the runs presented in the examples are conducted in a tubular continuous flow reactor operating at 115 psig (793 kPa gage). Reactor effluents are analyzed by gas-liquid chromatography. Generally, carbon monoxide is continuously injected at about 30 cc/minute STP into hydrogen flowing at about 90 cc/minute STP to obtain the synthesis gas feed in about stoichiometric molar proportions of reactants, i.e., $H_2/CO$ molar ratio of 3 or near 3. The catalysts are in the form of 16–60 mesh particles (U.S. Sieve Series).

Presentation of conversion data presents problems since widely different methane yields are possible for a given carbon monoxide conversion. However, since the $H_2/CO$ molar ratios are generally about 3, a formula proposed by the Institute of Gas Technology, Research Bulletin No. 31, page 10, is used to express the conversion of hydrogen and carbon monoxide to methane. This parameter which expresses conversion of the reactants to methane on an equal basis is defined in simplified form as follows:

$$\text{percent } CH_4 = 100 \left[ 4 \frac{\text{(moles dry product gas)}}{\text{(moles dry feed)}} \times \text{mole fraction } CH_4 \text{ in dry products gas} \right].$$

EXAMPLE I

A series of catalysts was prepared by aqueous impregnation of catalytic grade alumina particles, 16–60 mesh size, in each instance with a suitable amount of a single Periodic Group VIII metal nitrate solution. The metals employed were rhodium, palladium, ruthenium, iron, cobalt, and nickel. Each mixture was dried overnight at 125° C in an air oven. The uranium-promoted catalysts were prepared by impregnation of a portion of each of the previous, dried compositions with a suitable quantity of an aqueous solution of uranyl nitrate sufficient to give three weight percent uranium, calculated as the metal, based on the weight of the dry support containing the Group VIII metal compound. Each resulting mixture was then dried overnight at 125° C as before. About 5 grams of each catalyst was charged to the reactor and heated for two hours in hydrogen at 500° C at 115 psig, unless specified otherwise, cooled to 300° C, and the run started by injected sufficient carbon monoxide into the hydrogen stream to obtain a nominal $H_2/CO$ molar ratio of 3:1. A reactor pressure of 115 psig was maintained in each run. The temperature was generally raised in 50° C increments, allowing about 30 minutes at each temperature to reach steady-state conditions before sampling the effluent. After the 550° C reactor effluent was sampled, a hydrogen stream containing a known amount of hydrogen sulfide (ranged from 510 to 576 ppm) was substituted for the pure hydrogen stream previously used, and the mixture of hydrogen, hydrogen sulfide, and carbon monoxide contacted the catalyst at 550° C. Following the sulfiding, nominal 3:1 molar ratio of pure hydrogen and carbon monoxide again contacted the catalyst at 550° C to determine catalyst recovery properties.

The weight of catalyst used in each run, gaseous hourly space velocities of reactants, and calculated conversions to methane before sulfiding, after sulfiding, and after a specified recovery time are presented in Table I.

TABLE I

Methanation Activity of Unsulfided, Sulfided, and Recovered Group VIII Catalysts at 500° C

| Run No. | Catalyst, Wt.% Group VIII | U | Weight Catalyst Grams | GHSV, Reactants $H_2/CO$ | GHSV, Reactants $H_2/H_2S/CO$ | GHSV, Reactants $H_2/CO$ | Conversion to Methane, Percent Before Sulfiding | Conversion to Methane, Percent After Sulfiding | After Recovery % | After Recovery Hours | Remarks |
|---|---|---|---|---|---|---|---|---|---|---|---|
| 1 | Rh, 0.5 | 0 | 5.00 | 1105 | 1105 | 1105 | — | 32.0 | 57.7 | 11 | 1 |
| 1a | Rh, 0.5 | 3 | 5.21 | 1105 | 1105 | 1124 | 96.9 | 33.5 | 70.0 | 11 | 2 |
| 2 | Pd, 0.5 | 0 | 5.00 | 1010 | 1017 | — | 25.1 | 9.29 | — | — | 3 |
| 2a | Pd, 0.5 | 3 | 5.45 | 1064 | 1064 | 1064 | 17.6 | 6.91 | 8.64 | 13 | |
| 3 | Ru, 0.5 | 0 | 5.00 | 1122 | 1122 | 1097 | 100 | 7.76 | 42.1 | 11 | |
| 3a | Ru, 0.5 | 3 | 5.31 | 1078 | 1116 | 1088 | 100 | 9.98 | 31.4 | 11 | |
| 4 | Fe, 5.0 | 0 | 5.00 | 1067 | 973 | 1096 | 15.9 | 3.41 | 3.56 | 6.5 | |
| 4a | Fe, 5.0 | 3 | 5.00 | 1062 | 1062 | 1132 | 16.5 | 4.78 | 8.32 | 6.5 | |
| 5 | Co, 5.0 | 0 | 5.00 | 1074 | 1210 | 1122 | 90.4 | 3.60 | 23.6 | 11 | |
| 5a | Co, 5.0 | 3 | 5.00 | 1122 | 1103 | 1085 | 86.4 | 4.77 | 24.3 | 11.5 | |
| 6 | Ni, 5.0 | 0 | 5.62 | 1035 | 1025 | 1017 | 90.9 | 15.1 | 38.0 | 6.5 | |
| 6a | Ni, 5.0 | 3 | 5.95 | 1087 | 1100 | 1089 | 89.5 | 14.9 | 30.5 | 11.5 | |
| 7 | 0 | 10 | 5.13 | 1188 | — | — | 3.14 | — | — | — | |
| 8 | Rh, 0.5 | 0 | 4.80 | 1440 | 1360 | 1330 | 99.1 | 13.8 | 47.8 | 5.5 | 4 |

1 - Catalyst preheated one hour at 500° C.
2 - Recovery at 450° C after one hour gave 19.8 percent conversion of feed to methane and after 5.7 hours gave 20.2 percent. The 11-hour value in Table thus consisted of 5.7 hours at 450° C and 5.3 hours at 550° C.
3 - Catalyst preheated two hours at 550° C, recovery properties not determined.
4 - Catalyst preheated two hours at 550° C, catalyst support was calcium titanate.

Inspection of the data presented in Table I shows that active Group VIII catalysts for methanation under the conditions employed, in Runs 3, 5, 6, and 8, consist of rhodium, ruthenium, cobalt, and nickel with sulfur-free feeds. Alumina or calcium titanate are satisfactory supports. However, when the various catalysts are sulfided, the conversion results demonstrate that rhodium is superior to the others after poisoning, as well as in recovering from sulfur poisoning at methanation conditions with a sulfur-free feed.

When the catalyst contains three weight percent uranium as promoter, the data show that such catalysts obtain a nominal $H_2/CO$ molar ratio of 3:1. A reactor pressure of 115 psig was maintained in each run. The same procedure was followed as in Example I for raising the reactor temperature to 550° C, admitting $H_2S$ into the reactor, flushing with the $H_2/CO$ mixture, determining catalyst recovery properties and sampling each effluent at a specified time.

The weight of catalyst used in each run, gaseous hourly space velocities of reactants, and calculated conversions to methane before sulfiding, after sulfiding, and after a recovery time of 47 hours are presented in Table II.

TABLE II

Methanation Activity of Unsulfided, Sulfided, and Recovered Variable Rhodium-Containing Catalysts at 550° C

| Run No. | Catalyst, Wt. % Rh | Catalyst, Wt. % U | Weight Catalyst Grams | GHSV, Reactants $H_2/CO$ | GHSV, Reactants $H_2/H_2S/CO$ | GHSV, Reactants $H_2/CO$ | Conversion to Methane, % Before Sulfiding | Conversion to Methane, % After Sulfiding | Conversion to Methane, % After Recovery | Remarks |
|---|---|---|---|---|---|---|---|---|---|---|
| 1 | 0.25 | 0 | 4.77 | 1053 | 1015 | 1036 | 93.3 | 15.2 | 55.6 | 1 |
| 2 | 0.25 | 3.0 | 5.20 | 1014 | 1030 | 1046 | 47.7 | 21.5 | 60.4 | |
| 3 | 0.25 | 3.0 | 5.16 | 1039 | 1039 | 1039 | 43.2 | 23.6 | 66.6 | |
| 4 | 0.50 | 0 | 5.00 | 1169 | 1119 | 1159 | 89.3 | 25.9 | 64.1 | |
| 5 | 0.50 | 3.0 | 5.15 | 1337 | 1337 | 1243 | 85.5 | 30.4 | 71.1 | |
| 6 | 0.75 | 0 | 4.97 | 1097 | 1097 | 1088 | 92.7 | 32.7 | 63.4 | |
| 7 | 0.75 | 3.0 | 5.00 | 1105 | 1067 | 1067 | 95.7 | 36.0 | 77.0 | |
| 8 | 1.0 | 0 | 5.06 | 1212 | 1212 | 1189 | 93.1 | 31.4 | 78.1 | |
| 9 | 1.0 | 3.0 | 5.17 | 1170 | 1151 | 1141 | 100 | 41.7 | 79.3 | |

1 - Catalyst preheated two hours at 550° C in hydrogen.

are not appreciably helped in sulfur resistance as the sulfiding results on conversion show in Runs 1a, 2a, 3a, 4a, 5a, and 6a. Unexpectedly, the results in Run 1a show that recovery from sulfur poisoning is substantially enhanced for only the rhodium catalyst among the Group VIII catalysts tested. In addition, as footnote 2 explains, recovery must be effected at about 550° C under methanation conditions to obtain the good results. Recovery at 450° C is shown to give about 20 percent calculated conversion to methane after one hour and still only about 20 percent after 5.7 hours, suggesting little improvement with time can be expected. When the temperature is increased to 550° C, however, recovery reached 70 percent calculated conversion to methane with just 5.3 additional hours as the run continues.

EXAMPLE II

A series of catalysts containing variable amounts of rhodium in the absence or the presence of three weight percent uranium was prepared by aqueous impregnation of 16–60 mesh particles of catalytic grade alumina. The catalysts containing both rhodium and uranium were prepared by impregnation of the alumina with a single solution containing rhodium nitrate and uranyl nitrate. Each mixture was dried overnight at 125° C in an air oven as in Example I. About 5 grams of each catalyst was charged to the reactor, preheated at 500° C for two hours in hydrogen at 115 psig reactor pressure, cooled to 300° C and the run started by injecting sufficient carbon monoxide into the hydrogen stream to The data presented in Table II show in runs 1, 4, 6 and 8 that catalysts consisting of rhodium supported on alumina wherein the rhodium content ranges from 0.25 to 1.0 wt. % are excellent methanation catalysts under the conditions employed with a sulfur-free feed. The sulfided catalysts, especially when the rhodium content is at least 0.5 wt. %, still exhibit modest methanation activity at 550° C. When methanation is continued at 550° C with sulfur-free feed for 47 hours, the catalysts all recover substantially in conversion activity and in proportion to the rhodium content. Thus, the best recovery results are shown in run 8 with a catalyst containing 1 wt. % rhodium.

The effect of adding 3 wt. % uranium to the catalysts results in improved conversion of sulfided and recovered catalysts in each instance at all rhodium levels as runs 2, 3, 5, 7 and 9 show. When the uranium promoted catalysts are used only with sulfur-free feed, the results suggest that the rhodium content should be about 0.5 wt. % or more to achieve good methanation of the feed.

Runs 2 and 3 are duplicate runs. The results are considered to be in good agreement under the conditions employed.

EXAMPLE III

Another series of catalysts was prepared and evaluated for methanation in the manner described in Example II. In this series, each catalyst contained 0.5 wt. % rhodium and the uranium content was 0, 1.2, 3.0 and 5.0 wt. %. The results are presented in Table III.

TABLE III

Methanation Activity of Unsulfided, Sulfided, and Recovered Variable Uranium-Containing Catalysts at 550° C

| Run No. | Catalyst, Wt. % Rh | Catalyst, Wt. % U | Weight Catalyst Grams | GHSV, Reactants $H_2/CO$ | GHSV, Reactants $H_2/H_2S/CO$ | GHSV, Reactants $H_2/CO$ | Conversion to Methane, % Before Sulfiding | Conversion to Methane, % After Sulfiding | Conversion to Methane, % After Recovery | Remarks |
|---|---|---|---|---|---|---|---|---|---|---|
| 1 | 0.50 | 0 | 5.00 | 1169 | 1119 | 1159 | 89.3 | 25.9 | 64.1 | |
| 2 | 0.50 | 1.2 | 5.14 | 1128 | 1128 | 1128 | 58.0 | 27.0 | 69.2 | |
| 3 | 0.50 | 3.0 | 5.15 | 1337 | 1337 | 1243 | 85.5 | 30.4 | 71.7 | 1 |

TABLE III-continued

Methanation Activity of Unsulfided, Sulfided, and Recovered Variable Uranium-Containing Catalysts at 550° C

| Run No. | Catalyst, Wt. % Rh | Catalyst, Wt. % U | Weight Catalyst Grams | GHSV, Reactants $H_2/CO$ | GHSV, Reactants $H_2/H_2S/CO$ | GHSV, Reactants $H_2/CO$ | Conversion to Methane, % Before Sulfiding | Conversion to Methane, % After Sulfiding | Conversion to Methane, % After Recovery | Remarks |
|---|---|---|---|---|---|---|---|---|---|---|
| 4 | 0.50 | 5.0 | 5.46 | 1082 | 1082 | 1064 | 59.5 | 26.2 | 66.8 | 2 |

1 - Catalyst preheated 1-3/4 hours at 500° C in hydrogen.
2 - Catalyst preheated two hours at 550° C in hydrogen.

Inspection of the results presented in Table III shows the beneficial effects of uranium with rhodium catalysts on the performance of the sulfur poisoned catalyst for methanation activity after poisoning at 550° C. When methanation is continued at 550° C with a sulfur-free feed for 47 hours, the conversion results again demonstrate the importance of having uranium present in the catalyst. The results suggest that a uranium level of about 3 wt. % appears to be at or near optimum with 0.5 wt. % rhodium to provide a catalyst possessing reasonable methanation activity in an unpoisoned state and improved performance after poisoning and after recovery.

In summary, the methanation data show that at 550° C, superior results are obtained with a rhodium-containing catalyst as compared to other Group VIII elements after sulfur poisoning. Still more important, the data also show that the catalyst can be restored in activity in situ by continuing methanation at 550° C with a sulfur-free feed. The implication here is that loss of methanation activity caused by the accidental entry of relatively large amounts of a sulfur compound into the feed thus poisoning the catalyst need not cause shut down to replace the catalyst when the conditions and catalysts of this invention are employed.

The performance of the rhodium catalysts is enhanced by incorporating some uranium in the catalyst. A good balance of properties at the most reasonable cost is obtained with a catalyst containing about 0.5 wt. % rhodium and 3 wt. % uranium.

I claim:

1. In a process comprising contacting a feedstream comprising carbon monoxide and hydrogen with a supported rhodium-containing catalyst, which has been heated in a hydrogen stream, under methanation reaction conditions such that said carbon monoxide and hydrogen in said feedstream are converted to methane, and in which there is a loss of methanation catalyst activity caused by entry of sulfur into the feed and poisoning of said catalyst, the improvement for restoring methanation activity in situ of the sulfur-poisoned catalyst which comprises contacting said sulfur-poisoned catalyst under methanation conditions with a sulfur-free feed of carbon monoxide and hydrogen at a temperature of about 550° C for a period of time sufficient to substantially restore the activity of said catalyst, and continuing methanation by contacting said catalyst having restored methanation catalytic activity with carbon monoxide and hydrogen under methanation conditions such that a predominant amount of said carbon monoxide and hydrogen is converted to methane.

2. A process according to claim 1 in which said rhodium-containing catalyst is promoted with from about 0.1 to about 10 weight percent uranium based on the weight of the metal plus rhodium plus the support.

3. A process according to claim 1 wherein said methanation reaction conditions include a temperature of about 200° C to about 600° C, a pressure in the range of about 0 to about 12,000 psig, a GHSV of about 200 to about 10,000, and a molar ratio of hydrogen to carbon monoxide of about 3.

4. A process according to claim 1 in which said support is a refractory particulate substrate selected from alumina, silica-alumina, and Group II titanates.

5. A process according to claim 1 wherein the amount of rhodium present in said catalyst ranges from about 0.05 to about 5 weight percent based on the weight of the metal plus support and the amount of uranium present and said catalyst is promoted with uranium in an amount ranging from about 0.1 to about 10 weight percent based on the weight of metal plus the rhodium plus the support.

6. A process comprising contacting a feedstream comprising carbon monoxide and hydrogen with an effective amount of a supported rhodium catalyst, which has been heated in a hydrogen stream and contains 0.05 to about 5 weight percent rhodium based on metal plus support and promoted with about 0.1 to about 10 weight percent uranium based on total weight of metals plus the support under methanation reaction conditions such that a predominant amount of said carbon monoxide and hydrogen in said feedstream is converted to methane.

7. A process according to claim 6 wherein said feedstream is contacted with said catalyst at a temperature in the range from about 200° C to about 600° C, a pressure in the range of about 0 to about 12,000 psig, a GHSV of about 200 to about 10,000, and a molar ratio of hydrogen to carbon monoxide of about 3.

8. A process according to claim 7 wherein said support is a refractory particulate substrate selected from alumina, silica-alumina, and Group II titanates.

9. A process according to claim 6 wherein a sulfur compound is also present in said feed in an amount sufficient to poison said catalyst and adversely affect catalytic conversion of reactant.

10. A process according to claim 9 for restoring catalyst activity in situ caused by sulfur poisoning by contacting said sulfur-poisoned catalyst under methanation conditions with a sulfur-free feed of carbon monoxide and hydrogen at a temperature of about 550° C for a period of time sufficient to substantially restore the activity of said catalyst.

11. A process according to claim 6 wherein the amount of rhodium present is about 0.5 weight percent and the amount of uranium present in said catalyst is about 3 weight percent.

* * * * *